United States Patent
Yao

(10) Patent No.: US 9,314,223 B2
(45) Date of Patent: Apr. 19, 2016

(54) MULTI-STAGE DIGITAL ULTRASOUND BEAMFORMER

(75) Inventor: Linxin Yao, Renton, WA (US)

(73) Assignee: SHENZHEN MINDRAY BIO-MEDICAL ELECTRONICS CO., LTD., Shenzhen (CN)

(*) Notice: Subject to any disclaimer, the term of this patent is extended or adjusted under 35 U.S.C. 154(b) by 1515 days.

(21) Appl. No.: 11/876,781

(22) Filed: Oct. 23, 2007

(65) Prior Publication Data

US 2009/0105592 A1   Apr. 23, 2009

(51) Int. Cl.
  *A61B 8/08* (2006.01)
  *G01S 7/52* (2006.01)
  *G10K 11/34* (2006.01)

(52) U.S. Cl.
  CPC .......... *A61B 8/0883* (2013.01); *G01S 7/52026* (2013.01); *G01S 7/52095* (2013.01); *G10K 11/346* (2013.01)

(58) Field of Classification Search
  CPC ...... A61B 8/0883; B65H 59/24; B65H 63/02; G01S 7/52026; G01S 7/52095; G10K 11/346
  USPC .................................................. 600/443, 447
  See application file for complete search history.

(56) References Cited

U.S. PATENT DOCUMENTS

| | | |
|---|---|---|
| 4,542,653 A | 9/1985 | Liu |
| 5,369,624 A | 11/1994 | Fukukita et al. |
| 5,388,461 A | 2/1995 | Rigby |
| 5,487,389 A | 1/1996 | Banjanin et al. |
| 5,544,128 A | 8/1996 | Kim et al. |
| 5,573,001 A | 11/1996 | Petrofsky et al. |
| 5,653,236 A | 8/1997 | Miller |
| 5,676,147 A | 10/1997 | Petrofsky et al. |
| 5,844,139 A | 12/1998 | Miller et al. |
| 5,984,869 A | 11/1999 | Chiao et al. |
| 6,029,116 A | 2/2000 | Wright et al. |
| 6,104,673 A | 8/2000 | Cole et al. |
| 6,110,116 A | 8/2000 | Wright et al. |

(Continued)

FOREIGN PATENT DOCUMENTS

| | | |
|---|---|---|
| EP | 0859242 A1 | 8/1998 |
| WO | 0049427 | 8/2000 |

OTHER PUBLICATIONS

Torbjørn Hergum, et al., "Parallel Beamforming Using Synthetic Transmit Beams," IEEE Transactions on Ultrasonics, Ferroelectrics, and Frequency Control., vol. 54, No. 2, Feb. 2007.

(Continued)

*Primary Examiner* — Katherine Fernandez
(74) *Attorney, Agent, or Firm* — Kory D. Christensen; Stoel Rives LLP

(57) ABSTRACT

Elements in an ultrasound array are activated according to a transmit beamformer to create a series of transmit beams. For each transmit beam, the first stage of a receive beamformer determines a plurality of primary receive beams. A second beamformer stage then computes secondary receive beams as a function of the primary receive beams that correspond to return signals from different transmit beams to a common receive beam origin. For example, each secondary receive beam may be calculated as a function of the weighted, time-delayed sum of the primary receive beams. At least one of the secondary receive beams is then output from the beamformer to be used in creating a displayed image.

12 Claims, 11 Drawing Sheets

(56) References Cited

U.S. PATENT DOCUMENTS

| | | |
|---|---|---|
| 6,245,016 B1 | 6/2001 | Daft et al. |
| 6,309,356 B1 * | 10/2001 | Ustuner et al. .............. 600/443 |
| 6,363,033 B1 | 3/2002 | Cole et al. |
| 6,447,452 B1 | 9/2002 | Liu et al. |
| 6,482,157 B2 * | 11/2002 | Robinson .................... 600/437 |
| 6,491,634 B1 | 12/2002 | Leavitt et al. |
| 6,666,823 B2 | 12/2003 | Yao |
| 7,011,632 B2 * | 3/2006 | Steinbacher et al. ......... 600/437 |
| 7,722,541 B2 * | 5/2010 | Cai .............................. 600/447 |
| 2002/0143253 A1 | 10/2002 | Robinson |
| 2006/0241490 A1 * | 10/2006 | Lazenby ...................... 600/472 |
| 2008/0125656 A1 | 5/2008 | Yao et al. |
| 2009/0182235 A1 * | 7/2009 | Robert et al. ................ 600/443 |

OTHER PUBLICATIONS

Office Action mailed Mar. 7, 2011 in U.S. Appl. No. 11/940,089, filed Nov. 14, 2007.

* cited by examiner

MULTI-STAGE DIGITAL ULTRASOUND BEAMFORMER

FIELD OF THE INVENTION

This invention relates to diagnostic ultrasound imaging in general, and to digital beamforming in particular.

BACKGROUND OF THE INVENTION

Description of the Related Art

The importance of diagnostic ultrasound imaging is widely recognized, and has grown as imaging resolution and the range of available uses and features have steadily increased. Once an expensive luxury available only in the best-equipped hospitals, diagnostic ultrasound imaging is now a commonly and almost routinely offered procedure even in some individual physician's offices.

Diagnostic medical ultrasound machines are among the most sophisticated signal-processing systems in the civilian world and among the few that can press modern processors to their performance limits. The quality of an ultrasound image is consequently directly affected by many factors relating to both the hardware involved and the routines used to generate the necessary pattern of ultrasonic signals transmitted into the body and to receive and process their echo returns.

FIG. 1 illustrates the main components of a standard ultrasonic imaging system. The user enters various conventional scan parameters into an input/output (I/O) unit 100, which may comprise conventional hardware, system software, and devices as a keyboard, knobs, a mouse, and/or buttons. The input unit is connected to a processing system 200, which will typically be an electrically connected and cooperating group of processors 210 such as microprocessors and digital signal processors with necessary system software such as, for example, an operating system. The I/O unit 100 may therefore not need any processing capability of its own but rather simply act as a peripheral device for the main processing system 200.

As in known systems, the processing system 200 sets, adjusts, and monitors the operating parameters of a conventional transmission control circuit 220. This control circuit 220 generates and applies electrical control and driving signals to an ultrasonic probe, that is, transducer 300, which includes an array 310 of electro-acoustic (usually piezoelectric, such as PZT) elements. As is well known in the art, the piezoelectric elements generate ultrasonic waves when electrical signals of the proper frequency are applied to them.

To create the ultrasonic signals that are transmitted into the body (an "interrogation region," or a "region of interest" 400), all or some subset of these elements are electrically excited at a given frequency and are individually phased and time-shifted relative to each element's position in the array in such a way that the in-phase portions of the signals form a coherent transmit (Tx) beam: The time delays are chosen such that the echo signals arriving from a desired angular direction add coherently, whereas those signals arriving from other directions do not add coherently and so tend to cancel each other out. The amplitudes of the excitation signals applied to the array elements are typically varied (apodized) to control the resulting beam width and to suppress side lobes. The aperture of the array may also be varied, that is, the "width" of the activated elements (not all elements are usually activated at once) may be changed, just as the aperture of a camera may be varied to affect focal depth and provide uniform lateral resolution.

The various known methods for activating the elements according to a particular signal profile to best image a given area are generally referred to as transmit beamforming. By changing the amplitude and phasing of the transmitted signals, the transmit beam can be not only focused at a particular depth, but also steered off-axis, that is, not perpendicular to the center element among those activated. In FIG. 1, for example, the transmit beam has been steered at an angle to the face of the array 310. Out-of-phase portions of the individual transmit signals will tend to cancel each other. The transmit beam typically converges at a focal depth, beyond which it once again diverges. The transmit beam is steered in the azimuth/lateral direction LAT and the elevation direction EL, and is focused in the depth/axial direction AX so as to concentrate the ultrasonic energy of the beam onto desired points, such as a structure 410, within the interrogation region 400.

After any reflecting structure in the interrogation region is insonified, the transducer is typically switched by a switching circuit 230 from the transmit mode to a receive mode, such that the ultrasound reflected back onto the array face from any structures 410 within the imaged area will cause the elements to create corresponding electrical signals. The ultrasound sensed by any particular element, however, will be a combination of all the ultrasound energy reflected back from anywhere in the imaged region, regardless of which elements the energy originated from. In the general case, each element will receive some ultrasound energy created by all elements that were energized to form the transmit beam. In the receive (Rx) mode, each element will therefore generate a time-varying signal that in practice will differ from that of all other elements' received signals. Again, however, the in-phase portion of the reflected energy will dominate. The problem is how best to determine just what these coherent portions are, that is, which sensed values at the different elements represent the return signal from the desired focal point that, with proper time delay, corresponds to the portions of the return signals at the other array elements. This process is known as receive beamforming and the primary task of a receive beamformer is to determine and sum the coherent signals from targets received by all the active Rx array elements.

As is well understood, the piezoelectric array elements 310 convert the small mechanical vibrations caused by the echo signal into corresponding radio-frequency (RF) electrical signals. Amplification and other conventional signal conditioning are then applied to the return signals by a reception controller 240. This processing includes various procedures as needed to identify the echo signals that correspond to each scanned element in the interrogation region and form the receive beam. The reception controller 240, all or part of which is normally integrated into the processing system 200 itself, also converts the ultrasonic, radio-frequency (RF) return signals (typically on the order of a few to tens of megahertz) into lower frequency ranges for processing. This is well known in the art of ultrasonic imaging. The reception control circuitry includes a receive beamformer, aspects of which are described in greater detail below. Note that the transmission and reception controllers (or, for that matter, the transmit and receive beamformers) so not have to be implemented as separate components but may be combined in whole or in part with respect to both their hardware and software.

In conventional B-mode scanning, each point within the interrogation region is then represented as an intensity (brightness) value. The interrogation region can therefore be represented as a discretized pattern (matrix) of brightness or signal intensity values, which are stored as frame data in a memory 250. Other scan modes, such as for Doppler imaging, create and store corresponding values.

The interrogation region is normally not in the same shape as what the user wants to see displayed; even when it is, the digital acoustic intensity values that make up the frame data are normally not in a form suitable for driving a conventional gray-tone or color display directly. The acoustic intensity values for a selected sub-set (scan plane) are then typically applied to a conventional scan converter 260, which converts the digital acoustic values into display intensity values that are suitable for use in driving a display device 120, which may be part of the I/O unit 100. The display device 120 typically includes a screen (for example, LED or CRT) that is divided into an X-Y (or polar) matrix or pattern of picture elements or "pixels" that make up an image that the user can view and interpret.

FIG. 2 illustrates the main components of a receive beamformer 500. The illustrated beamformer 500 is simplified for purposes of illustration and the sizes and distances are not to scale. For example, even a one-dimensional linear array will usually have scores or even hundreds of array elements and not just the eight shown in FIG. 2. Moreover, it is common not to activate all the ultrasound elements at once, but rather to activate predetermined sub-sets of them according to some pattern. In FIG. 2, the transmit beam is assumed to have been focused on a focal point FP; the lines from the point 500 back to the array elements represent the acoustic return signals, that is, the echoes of the transmitted ultrasound.

In the illustrated case, the focal point FP, for purposes of easy illustration only, lies perpendicular to the face of the uppermost array element. Assuming that the ultrasound is propagating through tissue that is at least substantially acoustically homogeneous, ultrasound energy of the transmit beam that is reflected back from the focal point FP will reach the uppermost array element before reaching the others. The dashed line 520 illustrates the travel of coherent ultrasound back towards the array elements 310; that is, line 520 illustrates the coherent portion of reflection of a transmit beam.

As the wavy lines 530 illustrate, the reflected ultrasound will cause each array element to generate a corresponding analog electrical signal. The dots on the wavy lines represent the instantaneous values that correspond to the values of received data from a respective one of the array elements. Usually after amplification by a bank of amplifiers 540, the analog signals from the electro-acoustic array elements 310 are converted into digital values by a bank of analog-to-digital converters 550, whose sampling rate is controlled by clocking circuitry 555.

A time series of the converted digital values is then usually buffered in first-in-first-out latches 560 (for speed, although they could be stored in other types of memory devices). In FIG. 2, each stored digital value is represented as a small square on the signal path within the latches 560. The solid (filled in) squares within the latches illustrate values corresponding to an echo from the same target.

The digital values are then processed in a processing module (570), which will generally involve the main processors 210 (FIG. 1) executing the computer-readable software code that defines not only the implemented beamforming routine, but also such procedures as may involve a dedicated processor part of the greater processor to form an output signal that represents the value to be assigned to the focal point, for example, a brightness value. The processing will usually include such procedures as time-gating, gain compensation, diffraction compensation, dynamic receive delay, dynamic receive aperture size control, and dynamic receive apodization.

Because of its importance in ultrasonic imaging, there is a constant effort in the industry to improve receive beamformers. There are, indeed, hundreds of technical papers and even issued patents on the subject. These include the following issued U.S. patents:

| U.S. Pat. No. | Title |
|---|---|
| 6,666,823 | Beam combination method and system |
| 6,491,634 | Sub-beamforming apparatus and method for a portable ultrasound imaging system |
| 6,447,452 | System and method for reduction of parallel beamforming artifacts |
| 6,363,033 | Method and apparatus for transmit beamformer system |
| 6,245,016 | Ultrasound imaging system having post-beamformer signal processing using deconvolution algorithm |
| 6,110,116 | Method and apparatus for receive beamformer system |
| 6,104,673 | Method and apparatus for transmit beamformer system |
| 6,029,116 | Method and apparatus for a baseband processor of a receive beamformer system |
| 5,984,869 | Method and apparatus for ultrasonic beamforming using golay-coded excitation |
| 5,844,139 | Method and apparatus for providing dynamically variable time delays for ultrasound beamformer |
| 5,676,147 | Ultrasonic receive beamformer with phased sub-arrays |
| 5,653,236 | Apparatus for real-time distributed computation of beamforming delays in ultrasound imaging system |
| 5,573,001 | Ultrasonic receive beamformer with phased sub-arrays |
| 5,544,128 | Multi-beam digital beamforming method and apparatus |
| 5,388,461 | Beamforming time delay correction for a multi-element array ultrasonic scanner using beamsum-channel correlation |
| 5,369,624 | Digital beamformer having multi-phase parallel processing |
| 4,542,653 | Apparatus and method for beamforming in an ultrasonic transducer array |

A conventional digital ultrasound beamformer usually generates one transmit beam, but receives multiple receive beams back, since the single transmit beam may reflect back from different structures. Conventional single-stage beamformers are usually able to process these multiple beams by applying dynamic receive delay, dynamic receive aperture size control and dynamic receive apodization. Even so, prior art beamformers fail to take into consideration certain information that can be obtained from multiple receive beams over multiple transmits.

SUMMARY

The invention provides an ultrasound imaging system that comprises a main processing system including at least one processor and at least one memory; an ultrasound probe that includes an array of electroacoustic elements. The array may be one-dimensional (linear or non-linear, that is, curved) or have a higher dimension, such as two-dimensional. A beamforming system includes a transmit (Tx) beamformer and a receive (Rx) beamformer. The transmit beamformer is provided for activating at least one element of the array to generate a series of transmit beams that insonify a region of interest. The receive beamformer includes a first stage that is provided, for each transmit beam, for determining a plurality of primary receive beams. The receive beamformer also includes a second stage (which may be implemented with the first stage as an integrated beamformer, or separately) provided for computing at least one secondary receive beam as a temporally aligned combination of at least two of the primary receive beams.

According to a related method of operation, at least one element of an electroacoustic array of elements is activated to generate a series of transmit beams that insonify a region of interest. For at least one of the transmit beams, a plurality of primary receive beams is then determined. A secondary beamformer stage then computes at least one secondary receive beam as a temporally aligned combination of at least two of the primary receive beams. An image may then be generated as a function of at least one of the secondary receive beams.

The secondary beamformer stage may temporally align the at least two primary receive beams that correspond to the ultrasonic return signals from different ones of the transmit beams but that are received on a common receive beam line (a line of ultrasound propagation that passes through a focal point and a corresponding beam origin on the array) and then compute each secondary receive beam as a function of the at least two temporally aligned primary receive beams. One example of a suitable function is the possibly weighted, time-delayed sum of the at least two primary receive beams. One example of temporal alignment comprises computing a time delay of at least one of the primary receive beams relative to another one of the primary receive beams.

One example of a method for computing the time delay comprises: simulating conditions corresponding to anticipated transmission conditions of a first prime beam; determining a first instant transmit pulse pressure field (700) for a transmit pulse on the first prime beam for the conditions at a specified time, which corresponds to a specified depth; determining the centers of the transmit pulse along at least one radius direction from a first beam origin (A) of the first prime beam; determining a first transit time (R0) between the first transmit origin (A) and an intersection (B) of the instant transmit pulse pressure field at the specified depth and the first prime beam; determining a second transit time (R1) between a second beam origin (C) and an intersection (D) of a second pulse pressure field for a second primary receive beam; determining a time differential as a predetermined function of the first and second transit times; and in computing at least one of the secondary receive beams, applying to the second primary receive beam a delay computed as a predetermined function of the time differential.

DETAILED DESCRIPTION

The multi-stage beamformer and its novel methods of operation according to the invention are described primarily with reference to a one-dimensional array (which may be linear or curved, or a one-dimensional subset of the elements of a higher-dimensional array, etc.), but the principles of the invention are not restricted to this and indeed a 2-D example is illustrated. The invention may be used with any array having any number of elements, as long as there are enough elements to allow for receive element/beam "overlap" as explained below.

Figure 3:
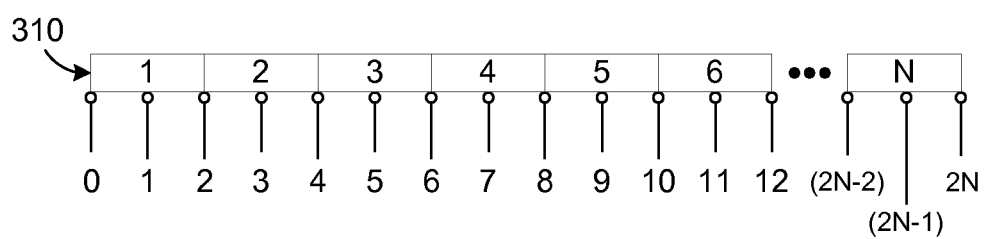
FIG. 3 illustrates the distribution of transmit beams in a one-dimensional array and in particular a numbering convention used to illustrate the principles of the invention.

To better understand the principles of the invention, assume that the invention is to be implemented with an N-element linear array, as is illustrated in FIG. 3. Transmit (Tx) beams may originate either at the center of an element or between two elements. For the purposes of illustration only, let the Tx beam with an origin between array elements (m−1) and m be numbered (2m−2); the beam with its origin in the center of element m be numbered (2m−1) and the beam with its origin between array elements m and (m+1) be numbered 2m. The beams with origins at the left and right edges of the array (viewed as in FIG. 3) are then labeled 0 and 2N, respectively. Thus, the transmit beam with its origin substantially between elements 4 and 5 is beam 8; the transmit beam with its origin substantially at the center of element 2 is Tx3; and so on. For an N-element linear array there will therefore in general be (2N+1) possible beam origins, for example 257 beam origins for a 128-element array.

Note that "origin" does not mean that the transmitted beam must be steered perpendicular to the array face from that point; thus, many transmit beams may originate from the same point, but may be steered to different angles and depths. Also, that a beam has its origin at a particular point does not necessarily define which array elements are used to generate the beam. For example, Tx5 could be generated by energizing array element 3 alone, or by activating elements 2-4, or just 2 and 4, or elements 1-5, or elements 1, 3 and 5, etc., all of which represent a symmetric combination of elements that has the enter of element 3 as the center of the combination. Even this symmetry is not necessary, however: It is also possible, using known methods, to calculate delays such that a particular Tx beam has an origin not at the center of the set of energized elements, that is, from an asymmetric pattern of elements. For example, Tx8 could also be determined when elements 1-15 are used to form the transmit beam.

How a particular transmit beam is generated will in general depend on such considerations as a desired aperture and apodization. This invention does not require any particular aperture, apodization, etc. as long as Tx mean origins can be determined. Another way to think of a beam origin is that it is the location at which the system computes the delays for all elements in the aperture. A beam is the line from the beam origin and through the focal point FP. This is true for both transmit and receive beams, although the direction of sound propagation will of course be reversed (to as opposed to from the focal point). An important calculation in both transmit and receive beamforming is the calculation of delays, and the beam origin is thus the point at which the delay is zero, meaning that other delays are measured relative to it. A delay length may then be defined as the difference between the length between an element to the focal point and the beam origin to the focal point.

The numbering convention illustrated in FIG. 3 may also be used to number receive beams. Note that it is not necessary for the same elements or even the same number of elements to be used to receive echo signals as are used to generate the transmit beam. This will again be a question of which aperture, etc., is applied. As one example, elements 1-4 could be energized to form Tx4, but then the signals received at elements 3-5 could be used to form a receive beam with zero or "origin" delay on line 7; thus, the system could transmit on Tx4 but "listen" on Rx7.

FIGS. 4*a*-4*j* illustrate how different primary receive beans are formed from two different transmit beams Tx8 and Tx12. Merely by way of illustration, the transmit beams are shown as being generated by four adjacent elements: elements 3-6 for Tx8 and elements 5-8 for Tx12. Similarly, it is assumed merely by way of example that the signals from three adjacent elements are used in the receive mode. For the sake of simplicity, it is also assumed that the transmit and receive lines are at the center of their respective groups of active elements. As explained above, these assumptions reflect just one of several possible choices. The elements used in the transmit are shown with a bold outline. The elements used for reception are indicated by a bracket above them and also an identification of their origin number below. Thus, in FIG. 4*a*, Tx8 is generated by elements 3-6, and reception is on elements 5-7, to form Rx11.

In the invention, the beam that is formed from the echo signals from a single transmit is referred to as the primary receive beam. The notation PB(i, j) is used here to indicate the primary receive beam that results from a transmit beam whose origin is i and that is received by any chosen group of elements whose receive beam origin is at position j, that is, reception is on line j.

Figure 4A:
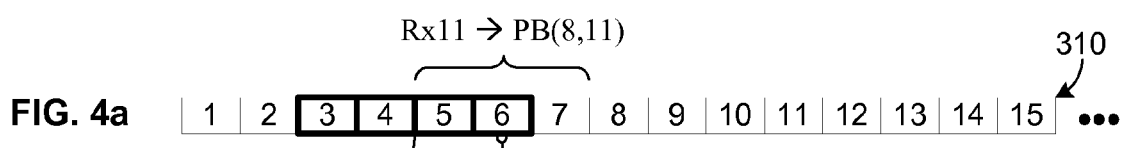
FIGS. 4a-4j illustrate one example of how a secondary series of primary receive beams may be formed from a series of transmit beams.
Figure 4B:
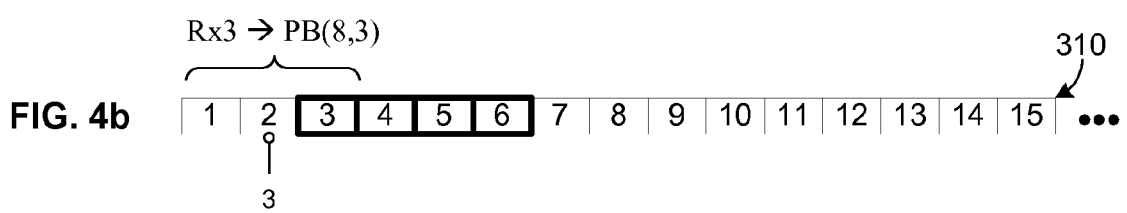
Figure 4C:
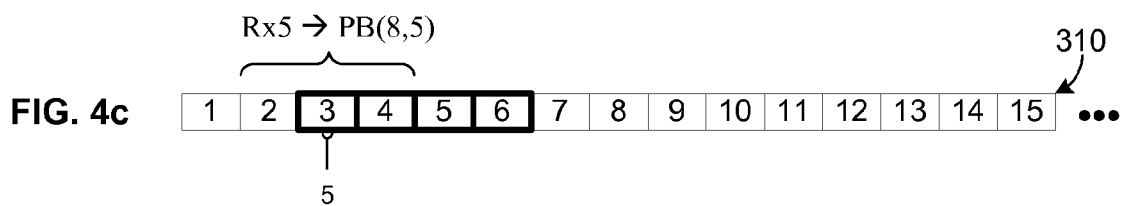
Figure 4D:
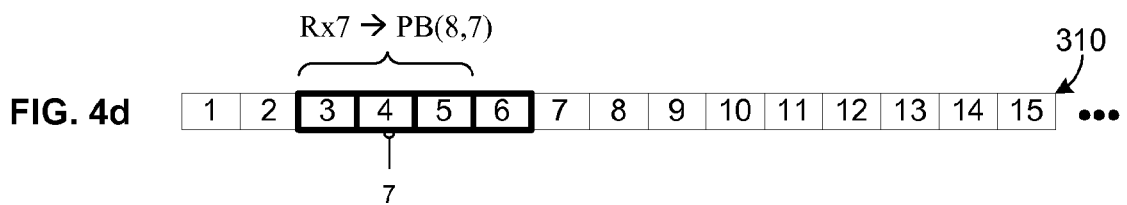
Figure 4E:
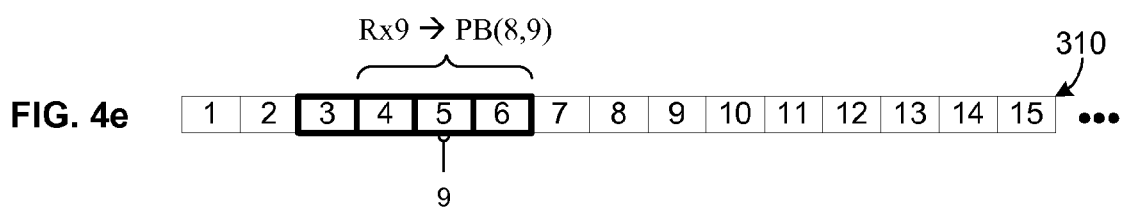

In FIGS. 4*a*-4*e*, the transmit beam is in each case Tx8, but the elements used to form five parallel receive beams from the same transmit of Tx8 shift from elements 1-3 (Rx3) to form PB(8,3) illustrated in FIG. 4*b*, to elements 2-4 (Rx5) to form PB(8,5) illustrated in FIG. 4*c*, to elements 3-5 (Rx7) to form PB(8,7) illustrated in FIG. 4*d*, to elements 4-6 (Rx9) to form PB(8,9) illustrated in FIG. 4*e*, to elements 5-7 (Rx11) to form PB(8,11) illustrated in FIG. 4*a*. Thus, the shift in receive mode is one element (two beam numbers) per receive beam.

Figure 4F:
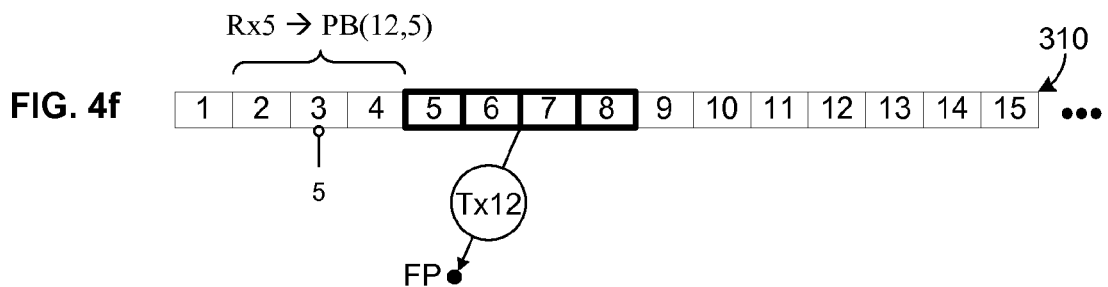
Figure 4G:
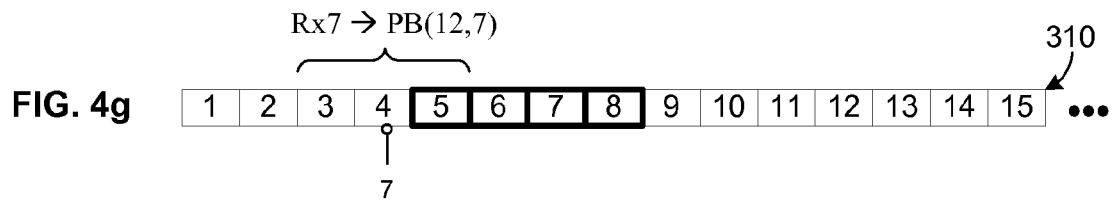
Figure 4H:
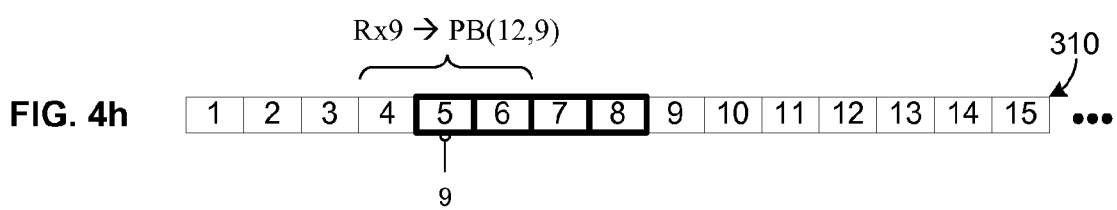
Figure 4I:
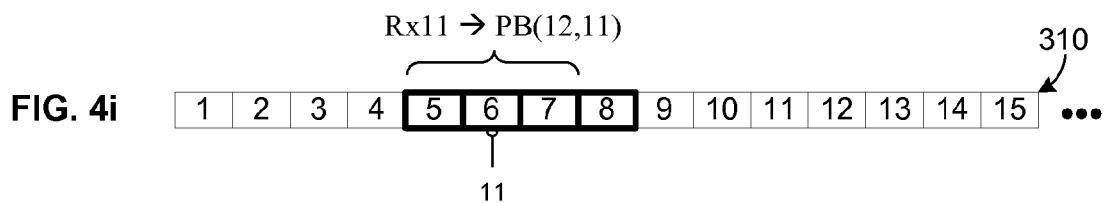
Figure 4J:
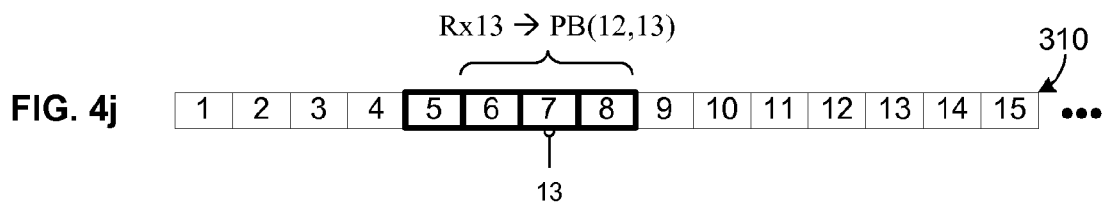

In FIGS. 4*f*-4*j*, the transmit beam is Tx12. Relative to what is illustrated in FIGS. 4*a*-4*e*, the transmit beam origin has thus been shifted to the right by four beam numbers (two elements). Note that, even for the same target, because of different Tx beams, the echo from this same target will be located at different depths of the prime beams, for example, on lines PB(8,5) and PB(12,5). The second-stage beamformer according to this invention (described in greater detail below) eliminates or at least substantially reduces this difference. In FIG. 4*f*, the elements used in the receive mode for Tx12 are elements 2-4 (Rx5) to form PB(12,5); in FIG. 4*g*, receive elements 3-5 (Rx7) form PB(12,7); in FIG. 4*h*, receive elements 4-6 (Rx9) form PB(12,9); in FIG. 4*i*, receive elements 5-7 (Rx11) form PB(12,11); and in FIG. 4*j*, receive elements 5-7 (Rx13) form PB(12,13). Thus, each subsequent primary receive beam in FIGS. 4*f*-4*j* is created by shifting two beam numbers (one element) to the right relative to the previous primary receive beam.

Figure 5:
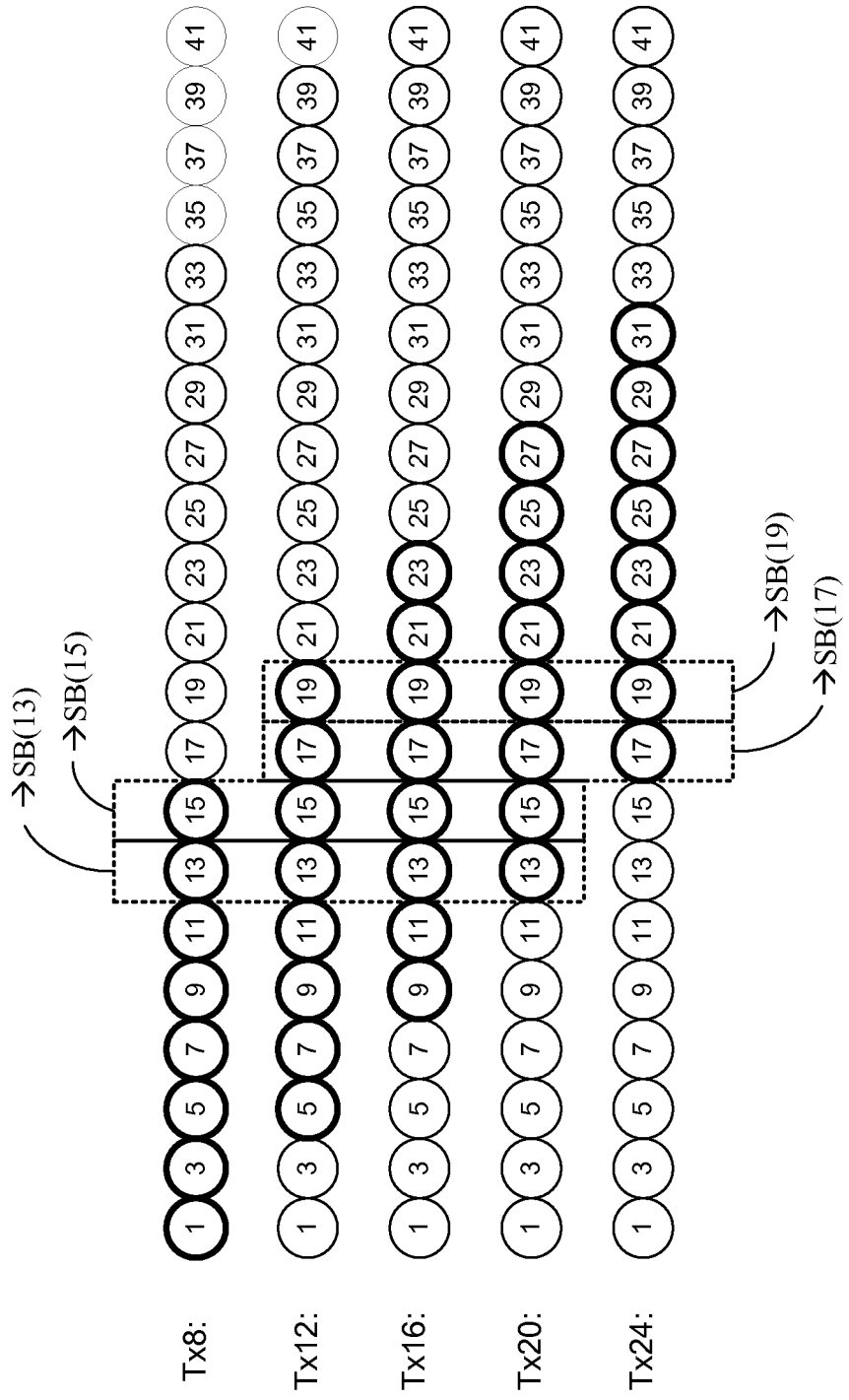
FIGS. 5 and 6 are two different representations of how primary receive beams from different transmits may align so as to form the basis for creating a secondary receive beam.

FIG. 5 illustrates one of many possible examples of a portion of an ultrasound scan. In FIG. 5, the numbered circles represent primary beams. In this illustrated case, eight primary beams are computed (in any known manner) for a Tx beam, then the aperture is "shifted" rightward (as illustrated in FIG. 5) by four beam numbers, a new transmit beam is formed and new receive beams are computed, then the aperture is shifted four more beam numbers to the right, and so on. FIG. 5 illustrates the activation pattern in receive mode for five transmit beams. Again just by way of example, five transmit beams Tx8, Tx12, Tx16, Tx20, and Tx24 are assumed. In FIG. 5, the darkened circles represent the primary receive beams that are computed for each respective transmit. Thus, the first transmit beam Tx8 results in primary receive beams PB(8,1), PB(8,3), PB(8,5), PB(8,7), PB(8,9), PB(8,11), PB(8,13), and PB(8,15). In table form, the primary receive beams for each of the five transmit beams is:

TABLE 1

| TX beam no. | Receive beam numbers |
|---|---|
| 8 | 1, 3, 5, 7, 9, 11, 13, 15 |
| 12 | 5, 7, 9, 11, 13, 15, 17, 19 |
| 16 | 9, 11, 13, 15, 17, 19, 21, 23 |
| 20 | 13, 15, 17, 19, 21, 23, 25, 27 |
| 24 | 17, 19, 21, 23, 25, 27, 29, 31 |
| ... | ... |

Figure 6:
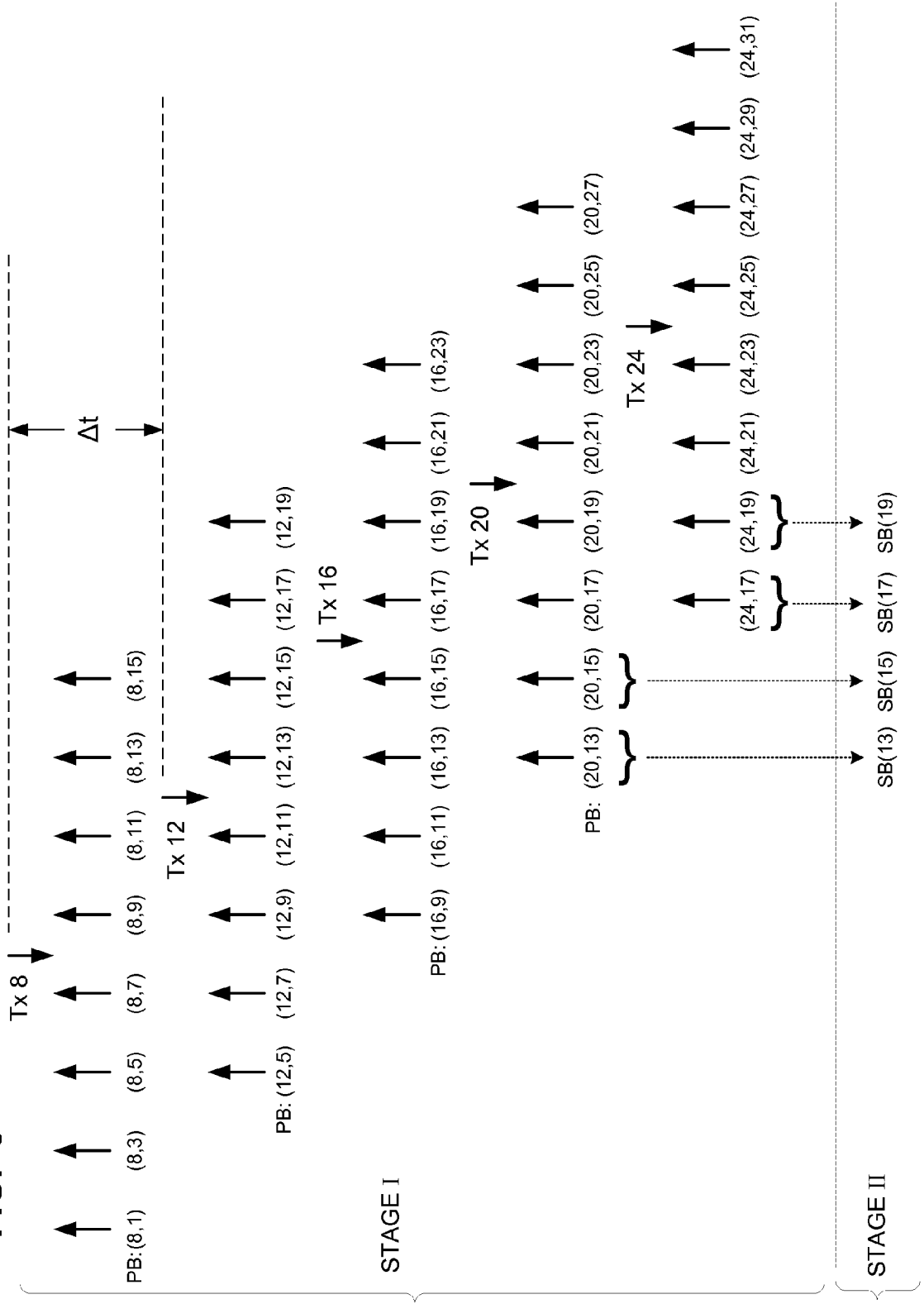

This is also illustrated in FIG. 6, which shows and labels the various receive beams for each transmit beam, where the transmit beams are separated in time by an amount Δt, which will be a function of the chosen frame rate. As FIG. 5, FIG. 6, and Table 1 show, several of the receive beams include information relating to the same insonified structure, but from different transmit beams. Thus, in this simple example, there are four separate values for primary receive beams 13, 15, 17 and 19. For primary receive beam 13, for example, there are the values PB(8,13), PB(12,13), PB(16,13) and PB(16,13), and for receive beam 19 there are values PB(12,19), PB(16,19), PB(20,19) and PB(24,19).

Defined in terms of beam numbers, if array elements corresponding to a span of n beam numbers are used in the receive aperture, and the aperture is shifted m beams on each transmit, then, except near the edges, there will be n/m primary beams for each beam location. The values of n and m will typically be design choices representing a trade-off between resolution and speed. Note that shifting can be defined in terms of either beam numbers or element numbers and that the numbering in either case is simply a matter of choice of convention.

The formation of primary beams is referred to here as the first or primary beamforming stage, which is labeled Stage I in FIG. 6. This invention provides for secondary beamforming that uses the information that conventional beamformers ignore. This secondary beamforming stage provides dynamic beamforming of the primary beams on the same line (as illustrated, having the same beam number).

The invention computes (using executable code stored on or in any suitable medium such as in the memory 250) secondary receive beams SB(p) as a function of the primary receive beams on line p. One suitable function is the weighted time-delayed sum of the primary receive beams PB(c,p), summed over all c (transmit beam numbers) for which there is a p (receive beam number) value. Expressed more abstractly:

$$SB(p)=f(PB(c,p),t)=\Sigma[w_c \cdot PB(c,p,t-\delta_c)]$$

where the sum is taken over c (all or a selected sub-set) for which there is a p value. Here, PB(c, p, t−$\delta_c$) is the primary receive beam PB(c,p) but that is time-delayed by an amount $\delta_c$ and weighted (possibly simply by unity, meaning no differential weighting at all) by the value $w_c$. In other words, the values of at least some of the primary receive beams received for different transmits but on the same beam are combined. Note that the summation is over the whole length of the beams, that is, over all time t in a chosen interval. Moreover, $w_c$ and $\delta_c$ may also be time- (depth-) dependent, and could have different values for different beams.

Thus, returning to the example above, SB(13) may be computed as the time-delayed, weighted sum of PB(8,13), PB(12,13), PB(16,13) and PB(16,13). In practice, what this means is that each secondary receive beam includes energy (information) from several transmit beams. Proper choices of aperture, shifting, transmit timing (all of which may be determined from case to case using known operating methods), and application of the invention should therefore lead to a synthesized, secondary receive beam that has less noise and is therefore clearer than any one of the primary receive beams processed in isolation.

As another example, assume as before that there are eight parallel Rx beams with a relative spacing of one element (two beam positions), but in this case assume that the shift per transmit is only two beam positions (one element) instead of four (two elements). Table 2 illustrates the correspondence between transmit and receive beam numbers:

TABLE 2

| Tx beam no. | Receive beam numbers |
|---|---|
| 8 | 1, 3, 5, 7, 9, 11, 13, 15 |
| 10 | 3, 5, 7, 9, 11, 13, 15, 17 |
| 12 | 5, 7, 9, 11, 13, 15, 17, 19 |
| 14 | 7, 9, 11, 13, 15, 17, 19, 21 |
| 16 | 9, 11, 13, 15, 17, 19, 21, 23 |
| 18 | 11, 13, 15, 17, 19, 21, 23, 25 |
| 20 | 13, 15, 17, 19, 21, 23, 25, 27 |
| 22 | 15, 17, 19, 21, 23, 25, 27, 29 |
| 24 | 17, 19, 21, 23, 25, 27, 29, 31 |
| 26 | 19, 21, 23, 25, 27, 29, 31, 33 |
| ... | ... |

It can be seen in Table 2 that from beam number 15 and up, there are eight primary beams for each beam location. To form the final, that is, secondary beam number 15, SB(15), is formed from the primary beams PB(8,15), PB(10,15), PB(12, 15), PB(14,15), PB(16,15), PB(18,15),PB(20,15) and PB(22, 15). All these eight primary beams will, as before, be time-delayed and weight-summed to align to an assumed beam whose transmit origin and receive origin are at the beam origin of beam 15.

In Table 2, observe also that for beam number 9, there are 5 primary beams for each beam location. To form the final beam number SB(9), the primary beams PB(8,9), PB(10,9), PB(12,9), PB(14,9) and PB(16,9) may be time-delayed and weight-summed. In other words, it is possible to have a different number of terms in the sum for different secondary beams; this will typically occur close to the edges of the array. It would also be possible simply not to perform secondary beamforming near the array edges if this is preferred over the additional programming burden. Once the secondary beams are computed, they may be passed on for further processing and display just as primary beams are in conventional beamformers.

Known theoretical and experimental methods may be used to determine the weights $w_c$, assuming that weighing is even implemented. For example, one might choose weights to deemphasize more off-axis primary beams. As another example, one might choose to deemphasize primary beams occurring relatively farther back in time, especially where the image region is itself moving, such as for cardiac imaging, as opposed to more static objects such as abdominal structures. These considerations should also be taken into account in determining the degree of shifting of active array elements—again, the more primary beams are accumulated, the better the secondary beam is likely to be, but the longer this will take, and faster scanning is usually preferred for dynamic regions such as the heart. In practice, the number of elements activated at a time and the degree of shift will be part of a trade-off: The greater the resolution desired, the longer it will take for processing.

Part of the computation of the secondary receive beams involves a determination of the dynamic time delays $\delta_c$ used to properly align the primary beams temporally in the SB(p) calculations to make sure they really represent the same beam line. In conventional transmit beamformer delay computations, the transmit time is usually computed as a function of geometry—the travel time of the Tx pulse from a Tx element to the Tx focal point, which is equal to the linear distance from the Tx element to the Tx focal point divided by the speed of sound. This assumes, however, that the acoustic wave pulse front is spherical, with the Tx element at the center; alternatively, these systems assume the Tx element to be a point source.

In the second stage of the two-stage beamformer according to the invention, the computations are based not upon signals from or to individual elements, but rather upon the prime transmit beams. In these delay computations, one should therefore also consider the transmit time which is the travel time of the Tx pulse from the Tx origin of the prime transmit beam to the Tx focal point. However, this travel time is not necessarily directly proportional to the linear distance from the Tx origin of the transmit beam to the Tx focal point divided by the speed of sound, because the wave front of the prime transmit beam is no longer necessarily spherical. One special case is where the transmit aperture of all the prime transmit beams is a single probe element; in this special case, geometrical calculations alone will typically suffice to compute the transmit delays. In general cases, however, the transmit apertures of prime transmit beams are a group of probe elements with a delay profile and an apodization; such an aperture cannot be viewed as a point source.

One way to compute the Tx delays $\delta_c$ of primary beams is through simulation of the instant Tx pulse pressure field of the transmit beams given knowledge of which type of body region (cardiac, abdominal, fetal, obstructing fatty tissue, etc.) the computations are to be used for, that is, what medium the ultrasound will pass though. The main steps of one example of such simulation include:

1. Set simulation conditions (either computationally or by using physical models) to match the actual Tx conditions of a primary beam. The conditions should include the probe geometry, the Tx pulse, Tx aperture size, Tx apodization, probe element directivity, tissue attenuation, the Tx focal location and others.

2. Set time (depth) to look, for example, at 50 μsec after the Tx; compute (or measure) the instant Tx pulse pressure field of this set of Tx conditions at the time specified.

3. Compute the centers of the pulse along the radius directions from the Tx origin. Draw (literally or computationally) a curve along the pulse centers on the 2-D Tx pressure field in 2-D image cases; or draw a surface along the pulse centers on the 3-D Tx pressure field in 3-D image cases.

4. Find the intersection of the pulse center curve and a transmit beam. Let $R_0$ be the distance (in time) from the Tx origin to the intersection.

5. Find the intersection of the pulse center curve and a primary beam. Let $R_1$ be the distance (in time) from the beam origin of the prime beam to the intersection. The primary beam delay for the second stage BF at this depth for this Tx beam is equal to the difference between the $R_0$ and $R_1$.

6. Compute the delay for all primary beams. This yields a delay profile at one depth.

7. Repeat steps 2-6 for every depth along the whole field to determine the dynamic Tx delay profiles for primary beams from one prime transmit beam. It maybe possible to reduce the computation by interpolation between computed depths.

8. Repeat steps 1-7 for all prime transmit beams to determine the Tx delay profiles for all primary beams from all prime transmit beams.

Figure 7:
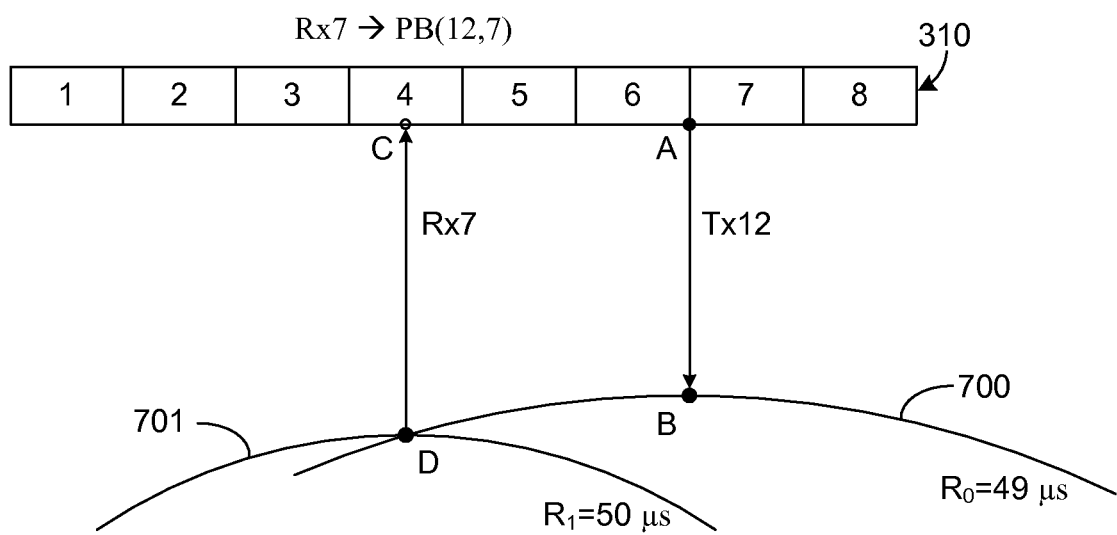
FIG. 7 illustrates the calculation of delay values used to form secondary receive beams.

As one simplified example, see FIG. 7. Assume a transmit beam Tx12 and a receive beam originating at beam origin 7, giving PB(12,7). Curve 700 represents the Tx pulse center 49 μs after transmitting. In FIG. 7, Tx12 beam origin is labeled A and the point of intersection of the curve 700 and Tx12 is labeled B. Let $R_0$ be the distance from A to B. In this example, $R_0$=49 μs. The beam origin of PB(12,7) is labeled C and the intersection of curve 700 and PB(12,7) is labeled D. Let $R_1$ be the distance from C to D, and assume by way of example that $R_1$=50 μs. Curve 701 illustrates an assumed pulse center 50 μsec from C. Now if the system were to use a beam having an origin at location 7 to see a target located at D, it would fire a transmit beam from C, the pulse would travel 50 μsec to D and will then reflect back to C for reception. This would correspond to a primary receive beam PB(7,7), whose round-trip time would thus be 50 μs+50 μs=100 μs. Using the two-stage beamformer, however, the system could fire Tx12, whose pulse originates at A, travels 49 μs and reaches the target at D. The echo from D will then take 50 μs from D to C for reception of the beam at location 7. In this case, the total round-trip time will be 49 μs+50 μs=99 μs. In the second stage of the beamformer, the system may therefore apply a 1 μs delay to PB(12, 7) at that depth to correct the Tx beam offset to generate a beam that appears like PB(7,7).

The two-stage beamformer according to the invention can be programmed flexibly in many ways to display various characteristics. In general, if the array and transmit controller are chosen and programmed so as to be able to form Np parallel beams from one transmit, and if Nt transmits are used to form an image, and if k primary beams are used to form one final, secondary beam, then the total number of final, secondary beams will be Nt*Np/k, since each transmit will give Np/k secondary beams.

If the frame rate is more important in a given application, one might, for example, configure the system such that k=2 to have Np/2 final beams per transmit. Thus, if Np=16, there will be eight final, secondary beams from one transmit, with few parallel artifacts due the second stage Tx beamformer of two primary beams. It would even be possible to set k=1 to form 16 beams per transmit (assuming by way of example that is the chosen aperture) to maximize frame rate, although at the cost of some parallel artifacts.

If image quality is of great importance, with Np=16 one could set k=16 to have a single final beam per transmit. Each secondary beam will then be formed dynamically formed from 16 primary beams; therefore, the final beams will have good Tx focusing along the depth.

For deep penetration, again with Np=16 as an example, one could also set k=16, yielding a single final, secondary beam per transmit. Each final beam may then be dynamically delay-summed from 16 primary beams, such that each final beam will comprise the acoustic power of 16 prime transmit beams. This should increase penetration roughly 12 dB for a 2.5 MHz probe, which translates into a significant increase of depth of around 4.8 cm.

Figure 1:
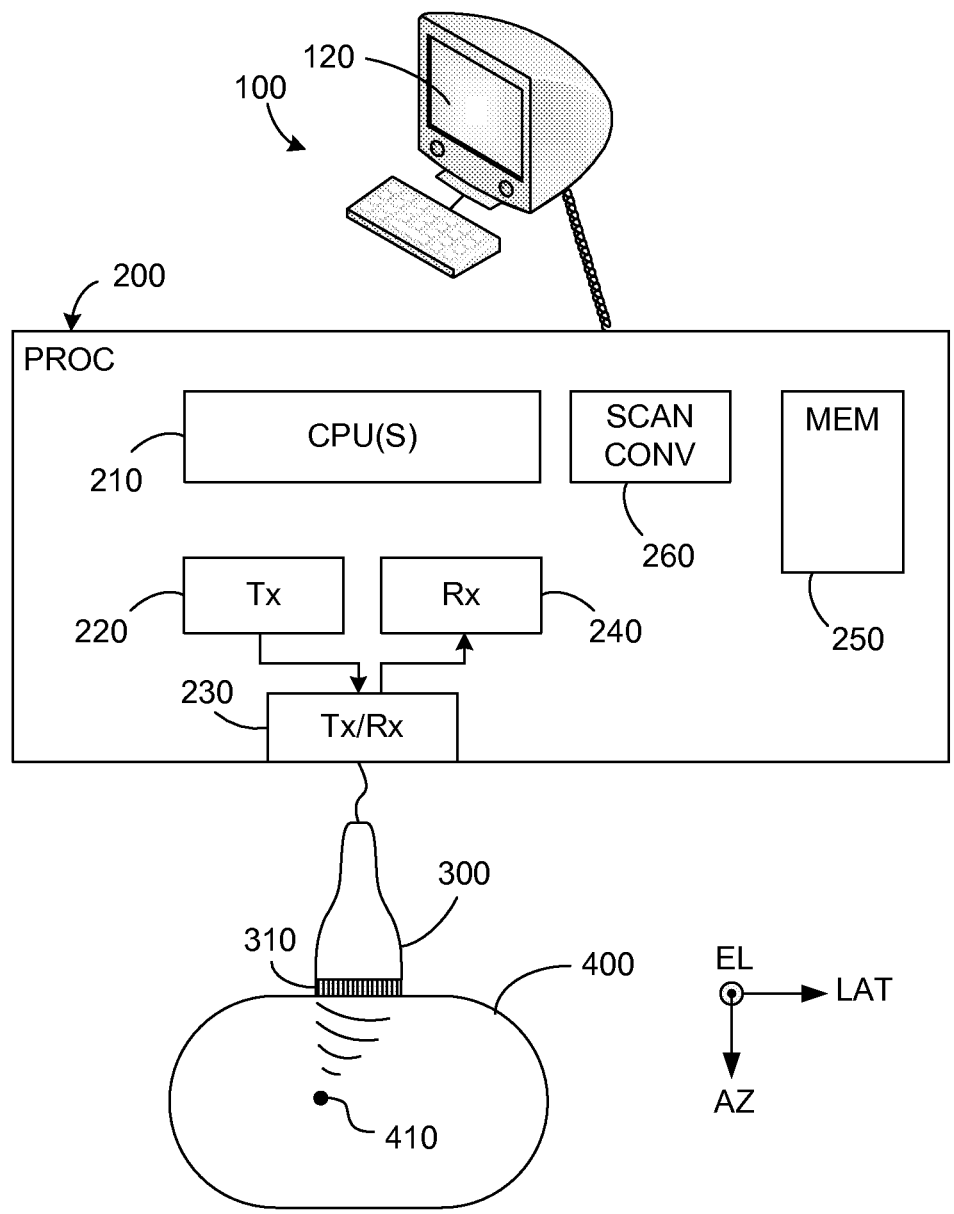
FIG. 1 illustrates the main components of an ultrasound imaging system as found in the prior art.
Figure 2:
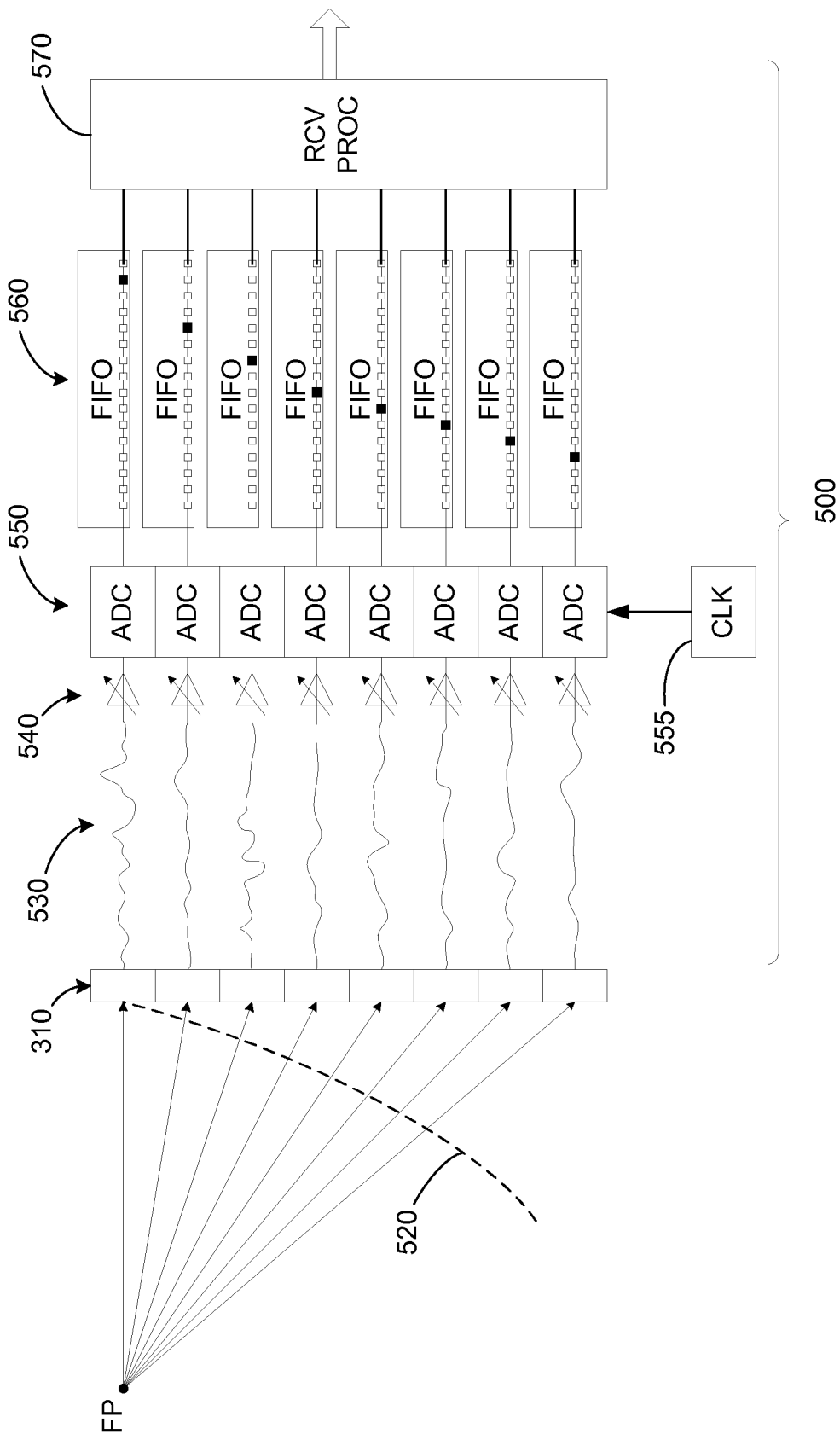
FIG. 2 illustrates the operation of a transmit and primary receive beamformer as in the prior art.
Figure 8:
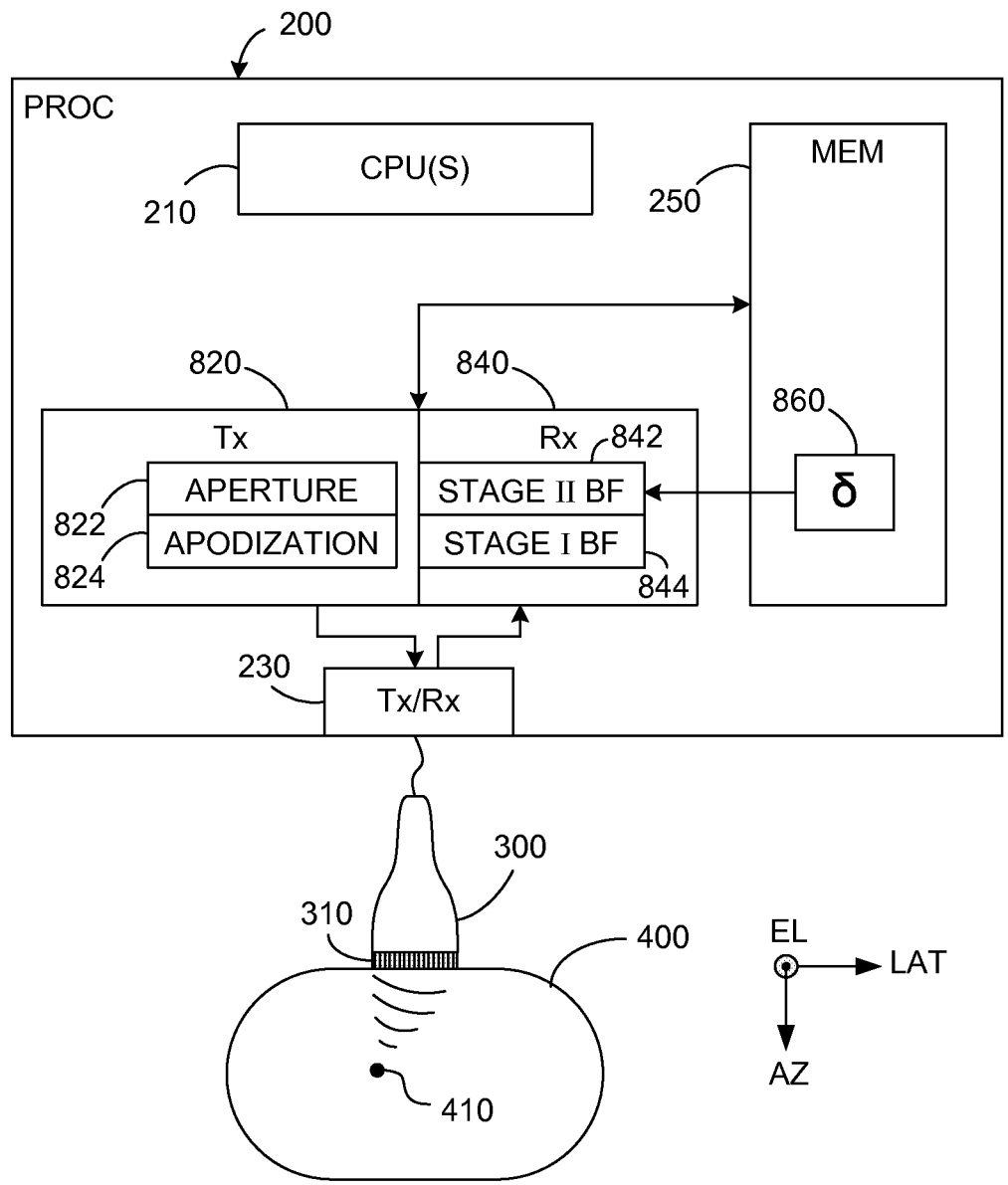
FIG. 8 illustrates the components of an ultrasound imaging system that includes two-stage beamforming.

FIG. 8, in which some components of FIG. 1 have been removed for clarity, illustrates how the Rx controller 840 includes both the first-stage and the second-stage beamformers 842, 844. Two common components of the Tx controller 820 are also illustrated, namely aperture and apodization controllers 822, 824.

It is not necessary to implement the two-stage beamformer of the invention as two hardware stages. It may, for example, prove practical to combine the second stage dynamic Tx delays into the first stage dynamic Rx delays. However, the first stage dynamic Rx delays can be computed as in the prior art as a function of geometry; this may be implemented using hardware calculators to reduce the need to transfer more control data. Computation of the delays $\delta_c$ for the second stage, however, is not as simple, as discussed above. These values may instead be pre-computed, pre-stored and loaded during live imaging from a table 860 stored either in the main system memory or in some other storage device; moreover, the values may be computed in real time, or off-line, or though a combination of both.

The computation of the SB(p) values may be accomplished in the second stage beamformer using a memory/accumulator, with a memory unit (either dedicated, for speed, or a portion of other memory such as the system memory) whose size is at least as big as needed to contain all the values defining the required number of beams, and at least equal to the maximum number of parallel beams per transmit. Once the SB(p) values are computed in the second receive beamformer stage, then these values may be passed on for subsequent conventional processing to form the basis of the display of the region of interest.

Figure 9A:
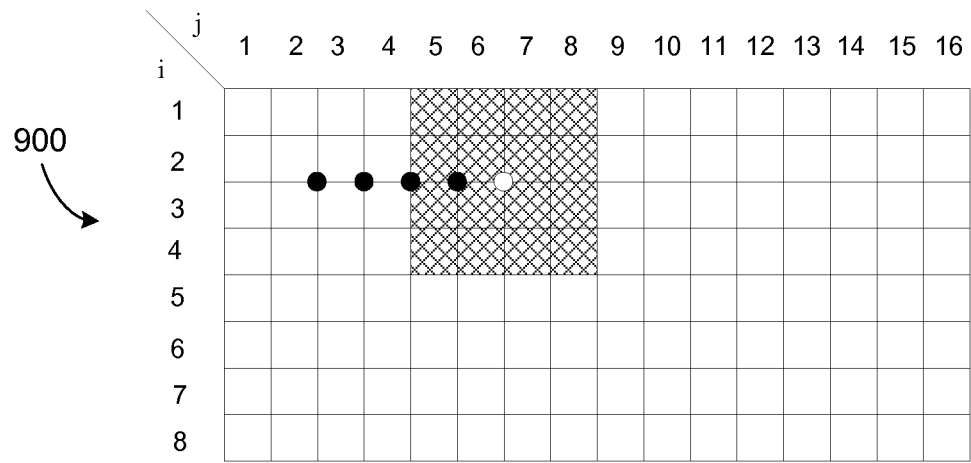
FIGS. 9a-9c illustrate two-stage beamforming for a two-dimensional array.

The principles of the invention may also be applied to higher dimensional arrays. FIG. 9, for example, illustrates a 8×16 element portion of a 2-D array 900, that is, with i=8 "rows" and j=16 "columns" of elements. Let E(i=a,b; j=x,y) represent the portion of the array comprising elements in rows a to b and columns x to y.

As in the one-dimensional case, beam numbers may also be defined to label the different possible origins of the transmit beams in the 2-D array. One possible numbering scheme for transmit beam origins for a 3-by-3 section (the upper left section, viewed as in FIG. 9a) of the 2-D array is illustrated in FIG. 9b, in which circles indicate beam origins and adjacent two-dimensional labels in parentheses indicate the beam numbers. Thus, beam number (3,3) (and thus the corresponding beam Tx(3,3) originating at the indicated point) is in the center of element E(2,2), beam number (4,5) is at the middle of the edge between E(2,3) and E(3,3), and so on. Other numbering schemes might, for example, not include any origin locations other than corners and centers of elements; the numbering scheme is simply a convention used here to illustrate the principles of the invention, although some numbering scheme will normally be adopted to make programming the software controlling the transmit and receive beamformers easier.

As mentioned above, partial or entire rows or columns of elements can be activated in a 2-D array such that they will in effect form 1-D arrays. This is not necessary either in general for diagnostic ultrasound imaging or in particular for implementing this invention; rather, the principles of the invention may be practiced in higher dimensions than just 1-D. By way of example, assume that a first transmit beam Tx(4,12) is formed from the shaded 4×4 subset of elements E(i=1,4; j=5,8), with a beam origin corresponding to beam number (4,12), which is shown as a small open circle. Assume by way of simplicity that a scan proceeds with a receive aperture chosen such that the first of the primary receive beams (indicated by solid dots) corresponds to the beam origin with beam number (4,4), then the aperture is shifted one element (two beam lines) in the j direction (to the right, viewed as in FIGS. 9a and 9b), a new primary beam is computed for beam number (4,6), then the receive aperture is again shifted one element to the right, another primary beam is computed for beam number (4,8), then the receive aperture is again shifted one element to the right, and another primary beam is computed for beam number (4,10).

PB[(ti, tj); (ra, rb)] may then be used to represent the primary receive beam that results from a transmit beam having the origin indicated by beam number (ti, tj) as received on the beam line with the number (numbered with the same scheme) (ra, rb). Thus, in the example given in the previous paragraph, for transmit beam Tx(4,12), primary beams PB[(4,12); (4,4)], PB[(4,12); (4,6)], PB[(4,12); (4,8)], and PB[(4,12); (4,10)] are computed in any conventional manner.

Figure 9C:
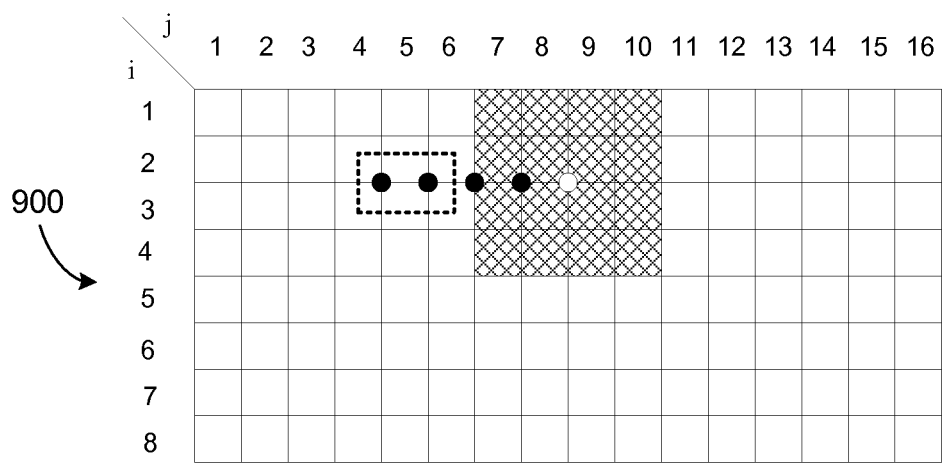
Figure 9B:
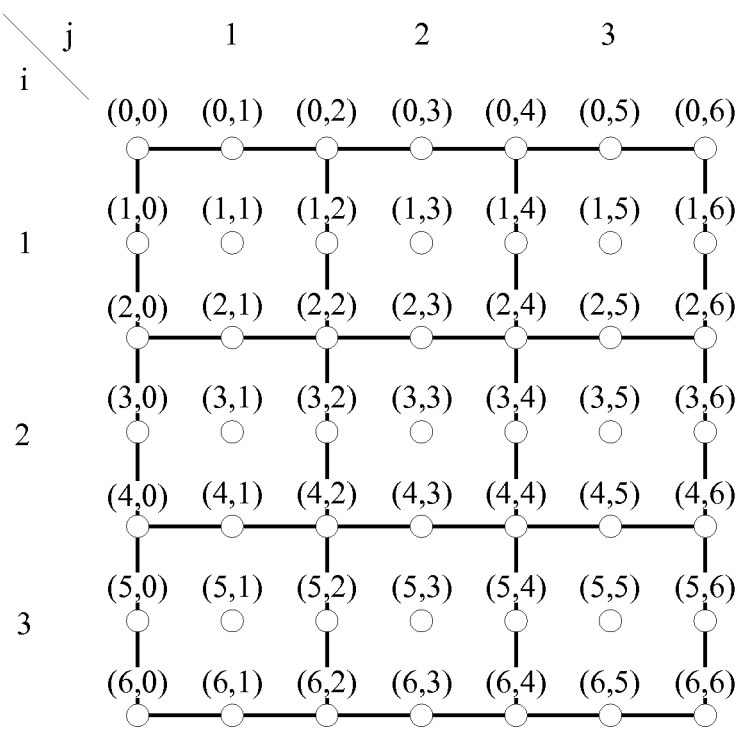

Now the transmit aperture may be shifted, for example, two elements (four beam numbers) to generate a transmit beam Tx(4,16) from the origin at beam number (4,16), indicated in FIG. 9c by the open circle at the center of the shaded aperture region elements E(i=1,4; j=7,10) Using the same pattern for receive beams as before (indicated again by solid dots), four primary receive beams can be computed for PB[(4,16); (4,8)], PB[(4,16); (4,10)], PB[(4,16); (4,12)], and PB[(4,16); (4,14)].

In this simple example, primary receive beams PB[(4,12); (4,8)] (from the first transmit) and PB[(4,16); (4,8)] (from the second transmit) both are primary receive beams on the same beam line, namely (4,8). The same applies to PB[(4,12); (4,10)] and PB[(4,16); (4,10)] on beam line (4,10). Each of these pairs may then be combined into a single secondary receive beam SB(4,10) as a weighted (again, even by unity), time-delayed sum. These "overlapping" receive beams are marked in FIG. 9c by being surrounded by a dashed rectangle.

It is not necessary for the shifting of either transmit or receive apertures to be in either the azimuthal or elevational direction alone. Even if shifting of one or the other, or both, contains a "diagonal" component, as long as more than one primary receive beam is formed for the same beam line, then these beams may be combined into a secondary beam. The degree of shifting on successive transmits and receives will in general determine the degree of "overlap" and thus how many terms (primary receive beams) are combined to form a single, corresponding secondary receive beam.

This invention provides a multi-stage beamformer (with features relating to both transmit and receive beamforming) that addresses several of the weaknesses of the prior art: It can candle a large number of parallel receive beams from a single transmit. In the second stage, it enables dynamic transmit focusing, dynamic transmit aperture size control and dynamic transmit apodization. Depending on some of the choices of parameters described above, such as aperture, degree of overlap, etc., this beamformer may also allow for an increased the frame rate. It also may improve the transmit beamformer quality and more fully use the acoustic available power.

What is claimed is:

1. An ultrasound imaging method comprising:
    activating at least one element of an electroacoustic array of elements to generate a series of transmit beams that insonify a region of interest;
    performing a receive beamforming process with a receive beamformer, wherein the receive beamforming process comprises:
        for each of at least two of the transmit beams of the series of transmit beams, determining a plurality of primary receive beams, and
        computing at least one secondary receive beam as a temporally aligned combination of at least two of the primary receive beams corresponding to different transmit beams of the at least two of the transmit beams,
        wherein the computing of the at least one secondary receive beam comprises applying dynamic, depth-dependent time delays to temporally align the at least two of the primary receive beams by computing the time delay of at least one of the primary receive beams relative to another one of the primary receive beams, wherein computing the time delay includes:
            simulating conditions corresponding to anticipated transmission conditions of a first prime transmit beam;
            determining a first instant transmit pulse pressure field for a transmit pulse on the first prime transmit beam for the conditions at a specified time, which corresponds to a specified depth;
            determining centers of the transmit pulse along at least one radius direction from a first beam origin of the first prime transmit beam, wherein the centers of the transmit pulse are determined based on locations of pulses from a plurality of transducer elements;
            determining a first transit time between the first transmit origin and an intersection of the instant transmit pulse pressure field at the specified depth and the first prime transmit beam;
            determining a second transit time between a second beam origin and an intersection of a second pulse pressure field for a second primary receive beam of the at least two of the primary receive beams; and
            determining a time differential as a predetermined function of the first and second transit times; and
            in computing at least one of the secondary receive beams, applying to the second primary receive beam a dynamic, depth-dependent delay profile computed as a predetermined function of the time differential, and
        wherein the at least two of the primary receive beams comprise primary receive beams with a same focal point and a same receive beam origin; and generating an image as a function of the at least one secondary receive beam.

2. The method of claim 1, wherein at least one of the plurality of primary receive beams is computed as a function of signals received at a plurality of electroacoustic elements.

3. The method of claim 1, further comprising computing each secondary receive beam as a function of a time-delayed sum of the at least two of the primary receive beams.

4. The method of claim 3, further comprising weighting a contribution of each primary receive beam in the sum.

5. The method of claim 4, wherein weights are time-dependent.

6. An ultrasound imaging system comprising:
    a main processing system including at least one processor and at least one memory;
    an ultrasound probe that includes an array of electroacoustic elements;
    a beamforming system including a transmit beamformer and a receive beamformer;
    in which:
    the transmit beamformer is provided for activating at least one element of the array to generate a series of transmit beams that insonify a region of interest;
    the receive beamformer includes a first stage that is provided for determining a plurality of primary receive beams for each transmit beam of the series of transmit beams;
    the receive beamformer includes a second stage provided for computing at least one secondary receive beam as a temporally aligned combination of at least two of the primary receive beams, wherein the second stage of the receive beamformer computes the at least one secondary receive beam as a temporally aligned combination of at least two of the primary receive beams by computing a time delay of at least one of the primary receive beams relative to another one of the primary receive beams, wherein computing the time delay is performed by:

simulating conditions corresponding to anticipated transmission conditions of a first prime transmit beam:

determining a first instant transmit pulse pressure field for a transmit pulse on the first prime transmit beam for the conditions at a specified time, which corresponds to a specified depth;

determining centers of the transmit pulse along at least one radius direction from a first beam origin of the first prime transmit beam, wherein the centers of the transmit pulse are determined based on locations of pulses from a plurality of transducer elements;

determining a first transit time between the first transmit origin and an intersection of the instant transmit pulse pressure field at the specified depth and the first prime transmit beam;

determining a second transit time between a second beam origin and an intersection of a second pulse pressure field for a second primary receive beam of the at least two of the primary receive beams; and determining a time differential as a predetermined function of the first and second transit times; and in computing at least one of the secondary receive beams, applying to the second primary receive beam a dynamic, depth-dependent delay profile computed as a predetermined function of the time differential, wherein the at least two of the primary receive beams comprise primary receive beams with a same focal point and a same receive beam origin, and wherein the at least two of the primary receive beams correspond to different transmit beams of the series of transmit beams; and the main processing system is provided for generating an image as a function of the at least one secondary receive beam and for creating corresponding signals for displaying the image on a display device.

7. The system of claim 6, in which the first stage is provided for computing at least one of the plurality of primary receive beams as a function of signals received at a plurality of electroacoustic elements in the array.

8. The system of claim 6, in which the second stage is further provided for computing each secondary receive beam as a function of a time-delayed sum of the at least two of the primary receive beams.

9. The system of claim 6, in which the array is a one-dimensional array.

10. The system of claim 6, in which the array is a two-dimensional array.

11. A beamforming system for ultrasound imaging comprising a transmit beamformer and a receive beamformer, in which:

the transmit beamformer is provided for activating at least one element in an array of electroacoustic elements to generate a series of transmit beams that insonify structures in a region of interest;

the receive beamformer includes a first stage that is provided, for each transmit beam of the series of transmit beams, for determining a plurality of primary receive beams;

a second stage provided for temporally aligning the plurality of primary receive beams that correspond to ultrasonic return signals from different transmit beams but that are received on a common beam line by applying dynamic, depth-dependent time delays to temporally align the plurality of primary receive beams, in which the common beam line is a line of ultrasound propagation that passes through a same focal point and a corresponding beam origin on the array, wherein temporally aligning the plurality of primary receive beams comprises determining centers of a transmit pulse along at least one radius direction from a first beam origin of a first transmit beam of the series of transmit beams, wherein the centers of the transmit pulse are determined based on locations of pulses from a plurality of electroacoustic elements, and for computing at least one secondary receive beam as a function of at least two temporally aligned primary receive beams, the at least one secondary receive beam being included in an output of the beamforming system, and wherein the at least two temporally aligned primary receive beams correspond to different transmit beams of the series of transmit beams.

12. The system of claim 11, in which the second stage is further provided for computing the at least one secondary receive beam as a function of a time-delayed sum of the at least two temporally aligned primary receive beams.

* * * * *